(12) United States Patent
Kallenbach et al.

(10) Patent No.: US 6,936,446 B2
(45) Date of Patent: Aug. 30, 2005

(54) LIGHT WEIGHT MEDIUM FOR GROWING MICROORGANISMS

(75) Inventors: Thomas J. Kallenbach, Bozeman, MT (US); Justin M. Buchanan, Bozeman, MT (US)

(73) Assignee: Eliminite, Inc., Bozeman, MT (US)

( * ) Notice: Subject to any disclaimer, the term of this patent is extended or adjusted under 35 U.S.C. 154(b) by 364 days.

(21) Appl. No.: 10/173,771

(22) Filed: Jun. 19, 2002

(65) Prior Publication Data

US 2003/0235896 A1 Dec. 25, 2003

(51) Int. Cl.$^7$ .................. C12N 11/08; C12N 11/14; C12N 11/02; C02F 3/00; C02F 3/32
(52) U.S. Cl. .................. 435/180; 435/176; 435/177; 435/243; 210/601; 210/606; 210/616
(58) Field of Search .................. 435/176, 177, 435/180, 243; 210/601, 606, 616

(56) References Cited

U.S. PATENT DOCUMENTS

| | | |
|---|---|---|
| 3,646,715 A | 3/1972 | Pope |
| 4,005,035 A | 1/1977 | Deaver |
| 4,781,781 A | 11/1988 | Hallworth |
| 4,983,299 A | 1/1991 | Lupton et al. |
| 5,000,853 A | 3/1991 | Reischl et al. |
| 5,217,616 A | 6/1993 | Sanyal et al. |
| 5,503,738 A | 4/1996 | DeFilippi et al. |
| 5,580,770 A | 12/1996 | DeFilippi |
| 5,590,449 A | 1/1997 | Chehab et al. |
| 5,863,789 A | 1/1999 | Komatsu et al. |
| 5,962,309 A | 10/1999 | Kumagai et al. |
| 6,077,424 A * | 6/2000 | Katsukura et al. .......... 210/151 |
| 6,293,045 B1 | 9/2001 | Morgan |
| 6,300,121 B1 * | 10/2001 | Davis-Hoover et al. . 435/262.5 |
| 6,326,191 B2 * | 12/2001 | VanToever ............... 435/299.1 |
| 6,617,155 B1 * | 9/2003 | Van Toever ................. 435/297 |

FOREIGN PATENT DOCUMENTS

| | | |
|---|---|---|
| DE | 3704802 A1 | 10/1987 |
| JP | 55-44866 A | 3/1980 |
| JP | 6-296500 A | 10/1994 |
| JP | 6-190385 | 12/1994 |

* cited by examiner

*Primary Examiner*—David M. Naff

(57) ABSTRACT

A light weight medium for growing microorganisms includes a mass of polymeric foam, such as a polyurethane foam, having an outer region enclosing an inner region. A plurality of fragments of an inorganic material, such as sand, are at least partially embedded in the outer region. The light weight medium may be used to support growth of microorganisms in a wide variety of biological and/or biochemical processes, or may be used without microorganisms in chemically treating wastes.

16 Claims, 1 Drawing Sheet

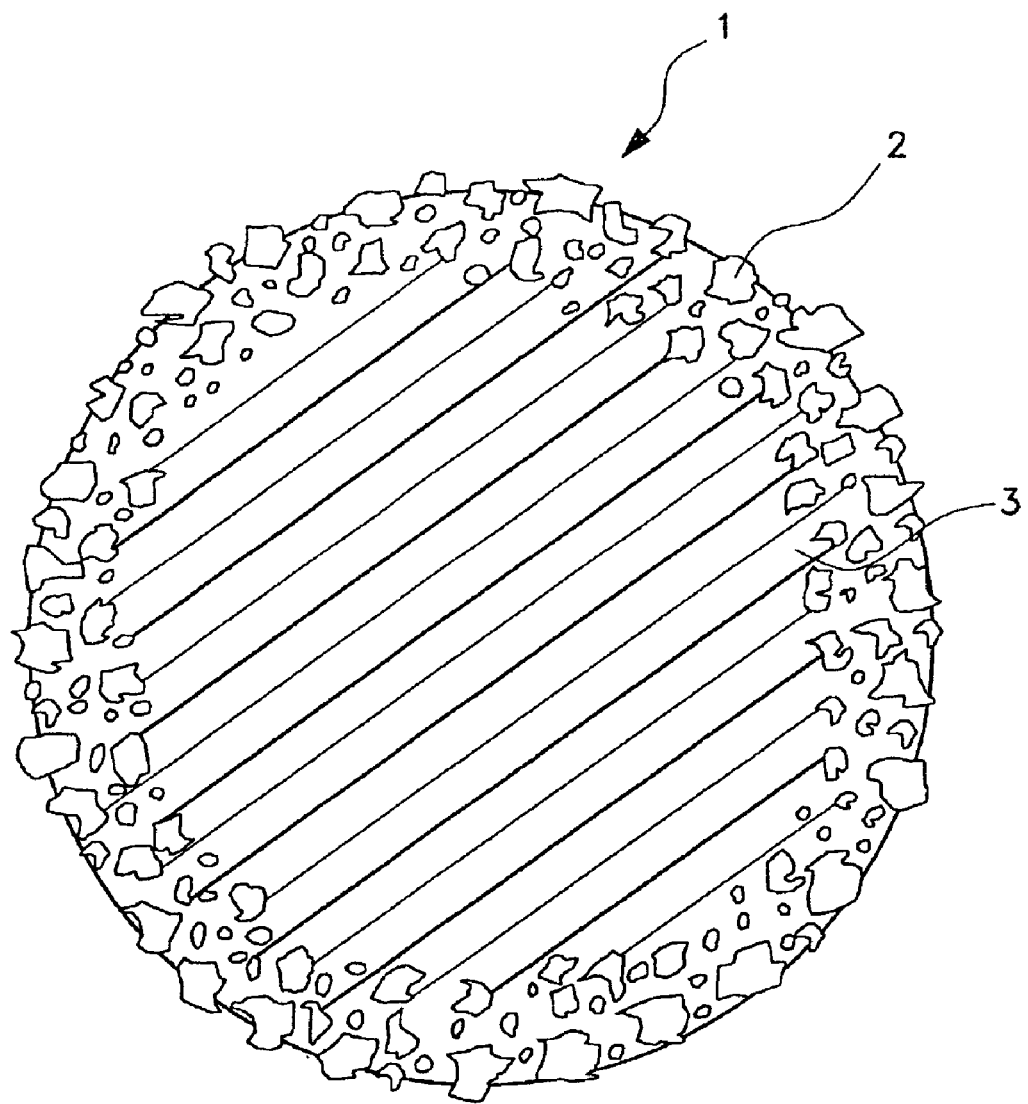

LIGHT WEIGHT MEDIUM FOR GROWING MICROORGANISMS

BACKGROUND OF THE INVENTION

1. Field of the Invention

The present invention relates to a solid carrier for supporting microorganism growth. More specifically, the present invention relates to: a solid, lightweight composite polymeric medium for supporting microorganism growth; a solid carrier useful in catalyzing chemical reactions and/or neutralizing acidic wastes; a solid, lightweight composite polymeric carrier useful in catalyzing chemical reactions and/or neutralizing acidic wastes.

2. Description of the Related Art

Solid carriers for supporting microorganism growth, also known as growth media, are used in a wide variety of industries such as wastewater treatment, production of organic compounds in bioreactors, gas separation, biofilters, remediation of hazardous waste, water treatment and production of fermented products. Some carriers provide an outer surface for attachment and growth of microorganisms while others allow growth on both the surface and on the inside of the carrier. Depending upon the intended purpose, the microorganisms, such as bacteria, algae and/or fungi, are used to either metabolize pollutants, synthesize specific organic compounds from chemical reactants, or ferment sugars into alcohols.

In wastewater treatment, raw sewage is processed into a stream of effluent safe enough to discharge into a body of water. After the raw sewage is subjected to a primary treatment stage in which some of the undissolved mass is allowed to settle out, leaving "primary" waste, the "primary" is then further treated in secondary and/or tertiary treatment stages, in which microorganisms are utilized to metabolize pollutants contained therein, resulting in conversion of complex organic matter into simpler organic compounds.

The treatment of the "primary" with microorganisms is often performed using one or both of two techniques: attached growth and suspended growth. In the attached growth process, microorganisms grow as a thick coat on a porous, immobilized support media known as trickling media. The waste stream is allowed to flow over or through the support medium, which is often shaped as a bed or column, so that the microorganisms are exposed to the pollutants for metabolization. Rock media is commonly used in such a manner.

While rock media does provide a suitable surface for the growth of microorganisms, it is quite dense at around 100 lb/ft$^3$, and thus, relatively expensive to transport. Other less dense support media, such as plastics, are less expensive to transport, more costly to manufacture, and present a non-polar surface which is not ideal as a media for promoting population by or with a polar substance, such as microorganisms.

In the suspended growth process, the microorganisms move freely about as flocs in a tank in which an influent stream constantly streams in and an effluent stream constantly flows out. In order to provide satisfactory treatment of the waste inside the tank, it is maintained in constant turbulence. Although the flocs are relatively lightweight, during periods of low flow through the tank the microorganisms will tend either to settle out or to wash out with the flow through the tank. As a result, the pollutants will not be metabolized into the simpler organic compounds due to a diminished concentration of organisms.

As noted above, solid growth media are used in many other processes, such as for the production of organic compounds in a bioreactor. In contrast to wastewater treatment, relatively pure strains of specialized microorganisms are employed which have the ability to synthesize specific organic compounds. However, much as in the trickling media process for wastewater treatment, microorganisms used for organic compound synthesis are immobilized upon a solid support in a relatively dense population. Likewise, this process also involves the same issues regarding transportation cost versus density of the solid growth media and cost of manufacturing the media.

In the remediation of hazardous waste sites, specific microorganisms are used that have the ability to metabolize specific hazardous pollutants into simpler organic compounds. In many gas separation processes, contaminated gases are passed through a sludge containing microorganisms which metabolize and thus remediate the pollutants. This type of bioremediation process is disclosed, for example, in U.S. Pat. Nos. 4,544,381 and 4,894,162. Similar to the suspended growth process used in secondary and tertiary wastewater treatment, low flow conditions tend to settle out or to wash out the microorganisms.

Another common method in gas separation processes for bioremediation is to pass contaminated gases through a bed of substrates in a bioreactor which carries microorganisms that degrade the pollutants contained in the gases. The prior art substrates used in this method have mainly been decomposable organic matters, such as peat, wood chips and other composts. However, the use of decomposable organic matters as the substrates for supporting and carrying the bioremediating microorganisms may be disadvantageous in that the substrates decompose and settle with time. Additionally, the organic substrates are not dimensionally stable over time. Such settlement and dimensional instability change the flow pattern of the gases fed through the bioreactor, creating undesirable flow patterns, and often create channeling that directs the influent gases to bypass substantial sections of the bioreactor, diminishing the efficiency of the reactor. Moreover, the organic substrates do not have appropriate configurations to allow the gases to pass through without a substantial pressure drop, and the organic substrates tend to get clogged as the biomass density increases in the reactor. Therefore, bioreactors employing current organic support materials require an increasingly high inflow pressure feeding the contaminated gases in order to overcome pressure losses created by the microbes populating the media.

Several solid carriers and polymeric composite products have been proposed for a variety of reasons. For example, Japanese Patent Publication JP 6-190385 discloses a bacterial carrier made by foaming an inorganically filled polyethylene or polypropylene. U.S. Pat. No. 5,503,738 discloses a macroporous substances coated with an adsorbent. U.S. Pat. No. 5,590,499 discloses an insulating wall element, wherein a mixture of sand and polyurethane fills in between regularly spaced brick fillets. Japanese Patent Publication Nos. JP 55-44866 and JP 6-296500, as well as German Patent Publication No. DE 37 04 802 A1, disclose other carriers and/or polymeric composite products. United States Published Patent Application Nos. US 2001/0002313 A1 (bioreactor media pellets) and US 2002/0015986 A1 (method for reducing the bioavailability of lead) disclose still other carriers and/or polymeric composite products. U.S. Pat. Nos. 3,232,865 (method for purifying wastewater), 3,646,715 (prefabricated building panel), 4,005,035 (high density rigid polyurethane foam products), 4,236,569 (foundry mold), 4,781,781 (solid polymeric material), 4,983,299 (removal of phenols from wastewater by a fixed bed reactor), 5,000,853 (biological treatment of sewage), 5,217,616 (removal of organic pollutants from water), 5,503,738 (biological remediation of vaporous pollutants), 5,863,789 (microorganism carrier for soil remediation), 5,962,309 (microorganism carrier for a fluidized bed) and U.S. Pat. No. 6,293,045 B1 (biodegradable mulch mat) disclose still other carriers and/or polymeric composite products.

None of the above inventions and patents, taken either singularly or in combination, is seen to describe the instant invention as claimed. Thus a light weight medium for growing microorganisms solving the aforementioned problems is desired.

SUMMARY OF THE INVENTION

The invention is a light weight medium for growing microorganisms. The medium includes a mass of polymeric foam, such as a polyurethane foam, having an outer region enclosing a core. The medium further includes a plurality of fragments, such as sand, of a treating material directly adhered to the polymeric foam on an outer surface of the outer region. A first portion of the fragments are adhered to the outer region, while a second portion of the fragments are at least partially embedded in the outer region and a third portion of the fragments are wholly embedded in the outer region. While the medium is particularly useful in supporting the growth of microorganisms, it may also be used in the absence of microorganisms, such as in the chemical treatment of wastes. The medium may be made by providing a plurality of fragments of a treating material, a not fully cured mass of polymeric foam, and applying the fragments to an outer region of the mass of foam.

Accordingly, it is a principal object of the invention to provide a microorganism growth medium that is lightweight.

It is another object of the invention to provide a microorganism growth medium that does not require an increasingly higher inflow pressure to overcome pressure losses created by the microbes populating the media.

It is a further object of the invention to provide a microorganism growth medium that will not settle out of a suspended growth process during periods of low flow, and retrofits the suspended growth process with a growth medium that supports an attached growth process.

Still another object of the invention is to provide a microorganism growth medium that is stable over time and will not decompose, rot or substantially change dimensions.

It is an object of the invention to provide improved elements and arrangements thereof for the purposes described which is inexpensive, dependable and fully effective in accomplishing its intended purposes.

These and other objects of the present invention will become readily apparent upon further review of the following specification and drawings.

BRIEF DESCRIPTION OF THE DRAWINGS

The single drawing FIGURE is cross-sectional view of a mass of polymeric foam with granular material embedded in an outer region thereof, according to the present invention.

DETAILED DESCRIPTION OF THE PREFERRED EMBODIMENTS

The present invention is a light weight medium for growth of microorganisms. While the medium, or carrier, is particularly suitable for supporting the growth of microorganisms, the medium, or carrier, may also be used without microorganisms. For example, the medium may used to provide a substrate having catalytic sites, and/or to provide a substrate having substances for neutralization of acids.

The medium offers many advantages over prior art microorganism support medium and prior art polymeric composite products. It is relatively lightweight, resulting in relatively low transportation costs as well as easy handling properties. The density of the medium may be varied in order to suit the desired function. For example, it may be made light enough to float in an aqueous environment or heavy enough to sink. Materials used for components of the medium may also be varied to suit the intended function. The medium's properties may be widely varied. Physical, electrical and chemical properties, such as surface area, chemical reactivity, conductivity, chargeability, etc. may be optimized by selecting the appropriate material. Again, depending upon the desired function, the medium may be rendered relatively chemically inert and stable over time. Finally, the medium is relatively inexpensive to manufacture.

As best shown in the FIGURE, the medium 1 includes a core of polymeric foam 3 and an outer region of a combination of a plurality of fragments of a treating material 2 and more polymeric foam 3. The treating material 2 includes fragments whose outer surface adheres to an outer surface of the polymeric foam 3 in the outer region, fragments of treating material 2 that are partially embedded in the foam 3 of the outer region, and fragments of treating material 2 wholly embedded in the foam 3 of the outer region. Preferably, no fragments are contained within the core, i.e., the core contains only foam and other suitable additives.

The polymeric foam 3 may be any foamable or foam-forming synthetic resin, including but not limited to: a polyurethane, a polystyrene, a polyolefin, copolymers thereof, and mixtures thereof. If a polyolefin is selected, a polyethylene, a polypropylene, their copolymers, or a mixture thereof is preferred. Preferably, the synthetic resin is a polyurethane or a polystyrene. More preferably, the polymeric foam 3 is polyurethane. Most preferably, the polymeric foam 3 is a polyurethane that is the reaction product of an organic isocyanate and any one of a wide variety of hydroxyl terminated polyols in the presence of a suitable blowing agent. In most cases, one should select a polymeric foam 3 able to withstand a temperature of up to 500° F. Otherwise, if the foam is to be used in an environment having a higher temperature, a high temperature foam may be substituted. When a polyurethane foam is selected as the polymeric foam 3, the medium 1 offers the advantages of low chemical reactivity, low density, low compressibility, stability over time, and resistance to rotting, decomposition and changes in physical dimensions.

Preferably the treating material 2 is an inorganic material. Many inorganic materials may be utilized, including any insoluble, or slowly soluble, hard material of small size. Such materials include, but are not limited to: sand, rock chips, limestone, $CaCO_3$, aluminum oxides, clay, textile fibers, activated carbon, pure elements (iron, aluminum, magnesium, etc.), and the like. Those skilled in the art will note that these materials are suitable for allowing localized electric charges on their surfaces, similar to surface characteristics of rock media, thereby attracting polar substances. They will also recognize that these materials have absorption and adsorption characteristics beneficial for supporting growth of microorganism. They will further recognize that the chargeable, adsorptive and/or absorptive characteristics of these materials result in an excellent source of sites for catalysis of chemical reactions.

When the medium 1 is used to treat wastes containing an undesirable level of phosphates, the treating material 2 preferably includes a material that reacts with the phosphates to produce a product that is more easily treated. For example, $CaCO_3$ will react with phosphates to produce calcium phosphates, while reaction with aluminum oxides will produce metal phosphates, or aluminum phosphates.

The size of the fragments of treating material 2 may be varied in order to suit the particular function of the medium 1 that is desired. For example, if a medium with a relatively low density is desired, the particle size of the treating material 2 is relatively small. Conversely, if a greater density is desired, the particle size of the granular material is increased. Also, if a larger total surface area of granular material is desired, the particle size of is increased. If a granular material of relatively large particle size is selected, better results for the medium are achieved if a foam of relatively greater density is employed. Otherwise, the higher weight of the granular material may tend to reduce adhesion between the polymeric foam and granular material, as well as overall strength and rigidity of the medium.

The particle size of the fragments of treating material is preferably in the range of from about 0.05 mm to about 15 mm. More preferably, the particle size is either from about 0.2 mm to about 2 mm. Another preferred particle size is from about 5.0 mm to about 14 mm. A particularly preferred treating material is sand having a particle size of from about 0.2 mm to about 2 mm. Another particularly preferred treating material is rock chip having a particle size of about ⅜" or less than ⅜".

The density of the medium 1 may be varied in order to suit the desired function. For example, if the medium 1 is used as a substitute for rock media, as described above, the density of the medium is from about 2 lb./ft³ to about 6 lb./ft³. Preferably, the density is from about 3 lb./ft³ to about 5 lb./ft³. Most preferably, the density is about 4 lb./ft³. Because of the much lower density, a tremendous difference in shipping costs may be realized. For example, conventional rock media can have a density of around 100 lb./ft³, while the particularly preferred density of the medium 1 is only 2% that of rock media. Additionally, the lighter medium 1 is much easier to handle and arrange. When the medium 1 is substituted for rock media, the relatively low density of the medium 1 allows a container housing it to be made from a wide variety of materials. In contrast, the relatively high density of rock media often requires that rock media be contained in a concrete or steel tank.

When the medium 1 is used to support growth of microorganisms during wastewater treatment, the microorganism selected depends upon the particular stage of treatment. In secondary treatment, microorganisms such as zoogloea ramigera, other heterotrophic bacteria, protozoa, rotifers, nitrosomonas and nitrobacter are used to reduce complex organic material in the waste stream into more easily treatable chemical compounds, such as water, carbon dioxide, nitrates and phosphates. In tertiary treatment, microorganisms such as pseudomonas, micrococcus, achromobacter, bacillus, lactobacillus, spirillum, hyphomicroblum, agrobacterium, acinetobacter, propionibacterium, rhizobium, corynebacterium, cytophagy, thiobacillus, and alcaligenes further reduce nitrates, nitrites and phosphorus into nitrogen, carbon dioxide and water.

When the medium 1 is used for supporting growth of microorganisms for uses other than wastewater treatment, such as in water treatment, bioremediation, production of organic compounds and fermentation, any of a wide variety of microorganisms may be used. Suitable microorganisms include but not limited to bacteria, algae, fungi and protozoa.

The medium 1 is also useful in processes not involving the growth of microorganisms, such as in mine drainage treatment and catalysis of chemical reactions. Watery mine wastes often include metals and salts that lower the pH to a level requiring it to be treated or neutralized before discharging it into a body of water in compliance with state and federal laws and regulations. For such wastes, the medium 1 preferably utilizes a caustic treating material 2 such as limestone which is useful in neutralization of the acidic waste.

The medium 1 may be made according to the following method. A depression is made in a bed of treating material 2, such as sand. The foam reactants, such as an isocyanate and an hydroxyl terminated polyol in the presence of a suitable blowing agent, are then allowed to foam in the depression. Treating material 2 is then applied to the less than fully cured foam. Application of the treating material 2 to the foam 3 is performed in such a manner so that none of the treating material 2 is introduced into the innermost portion of the foam 3. As illustrated in FIG. 1, the fragments of treating material 2 are randomly/irregularly distributed in the outer region of foam 3 in the finished product. The medium 1 thus formed is then allowed to fully cure. Finally, excess treating material 2 is removed from the medium 1. The shape of the medium 1 may be widely varied, such as a sphere, a cylinder, ovoid, a pancake, or combinations of the above. The inventors have found that the shape of the medium may be varied by controlling the shape of the depression by adjusting the humidity level in the environment surrounding the bed of treating material 2. The shape of the media 1 of the present invention increases water holding capacity when compared to conventional manufactured growth media. Channeling and flow through discrete paths is dramatically reduced in the growth medium 1 of the present invention. Surprisingly, it has also been found that no adhesive is necessary to adhere the treating material 2 to the polymeric foam 3, so additional steps of mixing in an adhesive found in some prior art products are not needed.

The medium 1 is not limited to the uses described above. For example, it may be used in distillation, air-scrubbing towers, flue gas scrubbers, animal waste treatment, aquarium treatment systems, pharmaceutical manufacturing, odor control at wastewater treatment plants (such as in a biofilter at the headworks of the plant) or manufacturing plants, biofilters, fluidized beds, catalytic beds and storm water treatment.

It is to be understood that the present invention is not limited to the embodiments described above, but encompasses any and all embodiments within the scope of the following claims.

We claim:

1. A lightweight carrier for supporting growth of microorganisms, comprising:
   a solid mass of polymeric foam having an outer region enclosing an inner region; and
   a plurality of fragments of treating material that adheres microorganisms, at least a portion of the fragments being directly adhered to an outer surface of said polymeric foam with none of the fragments being within said inner region.

2. The carrier of claim 1, wherein said polymeric foam is a synthetic polymer foam.

3. The carrier of claim 2, wherein said synthetic foam is a foam selected from the group consisting of: a polyurethane, a polyurethane copolymer, a polystyrene, a polystyrene copolymer, a polyolefin, a polyolefin copolymer, a polyethylene, a polyethylene copolymer, a polypropylene, a polypropylene copolymer, and mixtures thereof.

4. The carrier of claim 1, wherein said fragments of treating material have a particle size of from about 0.05 mm to about 15 mm.

5. The carrier of claim 1, wherein said fragments of treating material have a particle size of from about 0.05 mm to about 4 mm.

6. The carrier of claim 1, wherein said fragments of treating material have a particle size of from about 0.2 mm to about 2 mm.

7. The carrier of claim 1, wherein said fragments of treating material have a particle size of from about 4 mm to about 15 mm.

8. The carrier of claim 1, wherein said fragments of treating material have a particle size of from about 6 mm to about 13 mm.

9. The carrier of claim 1, wherein said fragments of treating material have a particle size of equal to or less than about 3/8".

10. The carrier of claim 1, wherein said carrier has a density from about 2 lb./ft$^3$ to about 6 lb./ft$^3$.

11. The carrier of claim 1, wherein said treating material is selected from the group consisting of: sand, limestone, aluminum oxide, and 3/8" rock chips.

12. The carrier of clam 11, wherein said treating material is sand.

13. The carrier of claim 12, wherein said treating material is sand having a particle size of from about 0.2 mm to about 2 mm.

14. The carrier of claim 11, wherein said treating material includes one of an aluminum oxide and an iron salt.

15. The carrier of claim 1, wherein a portion of said fragments of treating material are at least partially embedded in said outer region.

16. The carrier of claim 15, wherein a portion of said fragments of treating material are wholly embedded within said outer region.

* * * * *